(12) United States Patent
Cottam et al.

(10) Patent No.: US 10,857,122 B2
(45) Date of Patent: Dec. 8, 2020

(54) HYPOESTOXIDE, DERIVATIVES, RELATED COMPOUNDS, AND AGONISTS THEREOF FOR TREATMENT OR PREVENTION OF NEURODEGENERATIVE DISEASES

(71) Applicant: Immune Modulation, Inc., Bloomington, CA (US)

(72) Inventors: Howard Cottam, Escondido, CA (US); Emmanuel Ojo-Amaize, Fontana, CA (US); Emeka Nchekwube, Morgan Hill, CA (US); Olusola Oyemade, Rancho Cucamonga, CA (US)

(73) Assignee: IMMUNE MODULATION, INC., Bloomington, CA (US)

( * ) Notice: Subject to any disclaimer, the term of this patent is extended or adjusted under 35 U.S.C. 154(b) by 0 days.

(21) Appl. No.: 15/556,730

(22) PCT Filed: Feb. 3, 2016

(86) PCT No.: PCT/US2016/016294
§ 371 (c)(1),
(2) Date: Sep. 8, 2017

(87) PCT Pub. No.: WO2016/144441
PCT Pub. Date: Sep. 15, 2016

(65) Prior Publication Data
US 2018/0104211 A1    Apr. 19, 2018

Related U.S. Application Data

(60) Provisional application No. 62/177,187, filed on Mar. 9, 2015.

(51) Int. Cl.
*A61K 31/336* (2006.01)
*A61P 25/16* (2006.01)
*C07D 493/04* (2006.01)

(52) U.S. Cl.
CPC ........... *A61K 31/336* (2013.01); *A61P 25/16* (2018.01); *C07D 493/04* (2013.01)

(58) Field of Classification Search
CPC ...................................................... A61P 25/14
See application file for complete search history.

(56) References Cited

U.S. PATENT DOCUMENTS

| 5,801,193 A * | 9/1998 | Ojo-Amaize | C07D 493/08 514/232.8 |
| 6,001,871 A * | 12/1999 | Ojo-Amaize | A01N 43/20 514/475 |
| 6,514,984 B1 * | 2/2003 | Watanabe | A61K 31/403 514/224.5 |
| 7,910,333 B2 * | 3/2011 | Chilcote | C07K 16/18 435/69.7 |
| 9,724,399 B2 * | 8/2017 | Mandler | C07K 14/47 |
| 2004/0087553 A1 * | 5/2004 | Nchekwube | A61K 31/336 514/100 |
| 2010/0120853 A1 | 5/2010 | Cottam et al. | |
| 2010/0143945 A1 | 6/2010 | Khoshnan et al. | |
| 2010/0159015 A1 | 6/2010 | Burright et al. | |
| 2013/0052732 A1 | 2/2013 | Khoshnan et al. | |

FOREIGN PATENT DOCUMENTS

| WO | WO-2009103105 A2 * | 8/2009 | ............... A61P 25/00 |
| WO | WO-2010056223 A1 * | 5/2010 | ............ A61K 31/357 |
| WO | WO-2016144441 A1 | 9/2016 | |

OTHER PUBLICATIONS

Reagan-Shaw et al FASEBJ vol. 22 pp. 659-661, published 2007 (Year: 2007).*
Hunot , S. et al., (Annals of Neurology vol. 53 Supplemental 3 S49-S60 published 2003). (Year: 2003).*
Roy (PLoS One vol. 7 e38113 pp. 1-18. Published Online Jun. 18, 2012) (Year: 2012).*
Roy (PLoS One vol. 7 pp. e38113. Published Online Jun. 18, 2012) (Year: 2012).*
Hunot et al., (Annals of Neurology vol. 53 Supplemental 3 S49-S60 published 2003) (Year: 2003).*
Meredith et al (MPTP Mouse Models of Parkinson's Disease: J. Parkinson's Disease vol. 1 pp. 19-33 published 2011) (Year: 2011).*
Dehay et al., (Lancet Neurology vol. 14 pp. 855-866 published 2015). (Year: 2015).*
Clinical Trial NCT02095171 and NCT02157714 (Year: 2015).*
Clinical Trial NCT01568099 (Year: 2015).*
Clinical Trial NCT02157714 (Year: 2015).*
Esposito et al., Non-steroidal anti-inflammatory drugs in Parkinson's disease. Experimental Neurology, 205: 295-312, 2007.
Hunot et al., Neuroinflammatory processes in Parkinson's disease. Ann Neurol 53(Suppl. 3): S49-S60, 2003.
Paris et al. Inhibition of Abeta production by NF-kappaB inhibitors, Neurosci. Lett., 415:11-16, 2007.
PCT/US2016/016294 International Preliminary Report on Patentability dated Sep. 12, 2017.
PCT/US2016/016294 International Search Report and Written Opinion dated Jun. 2, 2016.
Roodveldt et al. Immunological features of alpha-synuclein in Parkinson's disease, J. Ceil. Mol. Med., 12(5B):1820-1829, 2008.
Wake et al., Microglia: actively surveying and shaping neuronal circuit structure and function. Trends Neurosci, 36(4): 209-217, 2013.

(Continued)

*Primary Examiner* — Timothy P Thomas
*Assistant Examiner* — George W Kosturko
(74) *Attorney, Agent, or Firm* — Wilson Sonsini Goodrich & Rosati

(57) ABSTRACT

New uses of hypoestoxide, its derivatives and related compounds for treatment and prevention of neurodegenerative diseases (e.g. Parkinsons disease, Alzheimers disease, Huntingtons disease) are described. More specifically, the invention relates to methods for treating various neurodegenerative diseases through administration of hypoestoxide, its derivatives and related compounds, or a combination thereof to a subject with a neurodegenerative disease such that the symptoms of the disease are treated or at least partially alleviated. Furthermore, the present invention further provides methods of preventing the development of neurodegenerative diseases in individuals who are predisposed to developing a neurodegenerative disease over time.

6 Claims, 13 Drawing Sheets

(56) References Cited

OTHER PUBLICATIONS

Wyss-Coray & Mucke, Inflammation in neurodegenerative disease—A double-edged sword. Neuron, 35(3): 419-432, 2002.
Bremner et al.: "Natural products as targeted modulators of the nuclear factor-κB pathway" Journal of harmacy and Pharmacology, 2002, pp. 453-472.
European Patent Application No. 16762089 Extended European Search Report dated Oct. 25, 2018.
Flood et al.: "Transcriptional Factor NF-κB as a Target for Therapy in Parkinson's Disease" Parkinson's Disease, vol. 2011, Article ID 216298, 8 pages (2011).
Hernán et al.: "Nonsteroidal anti-inflammatory drugs and the incidence of Parkinson disease" Neurology, vol. 66, 2006, pp. 1097-1099.
Kim et al.: "Hypoestoxide reduces neuroinflammation and α-synuclein accumulation in a mouse model of Parkinson's disease" Journal of Neuroinflammation, 2015, 10 pages.
Lee et al.: "Mechanisms of Parkinson's Disease Linked to Pathological α-Synuclein: New Targets for Drug Discovery" Neuron, vol. 52, Oct. 5, 2006, pp. 33-38.
Ojo-Amaize et al.: "Hypoestoxide, a Novel Anti-inflammatory Natural Diterpene, Inhibits the Activity of IκB Kinase" Cellular Immunology, vol. 209, 2001, pp. 149-157.
Paris et al.: "Inhibition of Aβ production by NF-κB inhibitors" ScienceDirect, 2007, pp. 11-16.
Ton et al.: "Nonsteroidal Anti-Inflammatory Drugs and Risk of Parkinson's Disease" Movement Disorders, vol. 21, No. 7, 2006, pp. 964-969.
McCormack et al.: Enhanced α-Syncuclein Expression in Human Neurodegenerative Diseases: Pathogenetic and Therapeutic Implications; Current Protein and Peptide Science; 10; pp. 476-482 (2009).
Driver et al.: Use of non-steroidal anti-inflammatory drugs and risk of Parkinson's disease: nested case-control study. BMJ 342: d198 (2011) 21 pages.
Lane et al.: Animal models of Parkinson's disease and L-dopa induced dyskinesia: How close are we to the clinic? Psychopharmacology 199: 303-312 (2008).
Manthripragada et al.: Non-steroidal anti-inflammatory drug use and the risk of Parkinson's disease. Neuroepidemiology 36(3): 155-161 (2011).
Potashkin et al.: Limitations of Animal Models of Parkinson's Disease. SAGE-Hindawi Access to Research Parkinson's Disease vol. 2011, Article ID 658083, 7 pages (2011).
Aubin et al.: Aspirin and salicylate protect against MPTP-induced dopamine depletion in mice. J Neurochem.71(4): 1635-1642 (1998).
Australian Patent Application No. 2016229520 Second Examination Report dated Aug. 25, 2020.
European Patent Application No. 16762089.7 Office Action dated Jul. 28, 2020.
Hirohata et al.: Non-steroidal anti-inflammatory drugs have potent anti-fibrillogenic and fibril-destabilizing effects for α-synuclein fibrils in vitro. Neuropharmacology 54(3): 620-627 (2008).
Clinical Trial NCT03100149.A Study to Evaluate the Efficacy of Prasinezumab (RO7046015/PRX002) in Participants With Early Parkinson's Disease (Pasadena). NIH U.S. National Library of Medicine. 9 pages total (2017) [Accessed on Oct. 19, 2020].

\* cited by examiner

HYPOESTOXIDE, DERIVATIVES, RELATED COMPOUNDS, AND AGONISTS THEREOF FOR TREATMENT OR PREVENTION OF NEURODEGENERATIVE DISEASES

CROSS-REFERENCE TO RELATED APPLICATIONS

This application claims the benefit of U.S. Provisional Patent Application No. 62/177,187, filed Mar. 9, 2015, which is hereby incorporated by reference in its entirety.

FIELD OF THE INVENTION

The present invention generally relates to hypoestoxide, its directives, and compounds related thereto. More particularly, the present invention is directed to the composition and method of using hypoestoxide, its derivatives, related compounds, or a combination thereof for inhibiting α-synuclein aggregation in the brain of an animal or human subject with a neurodegenerative disease.

BACKGROUND OF THE INVENTION

Alpha-synuclein is a main pathology of many neurodegenerative diseases such as Parkinson's disease (PD), Alzheimer's disease (AD), Lewy body dementia, Huntington's disease, Multiple Sclerosis (MS), and multiple system atrophy, among others. In this regard, human α-synuclein transgenic animal models have been shown to exhibit PD-like pathological and/or neurological alterations which include, but not limited to, impairment in motor performance and coordination, reduction in spontaneous activity, altered fine motor skills, and sensorimotor deficits.

An important challenge in the treatment of many neurodegenerative diseases, such as PD, is the need to deliver therapeutic drugs to the brain through the blood-brain barrier despite its poor permeability to drugs. Multiple efforts have been made to deliver therapeutic drugs to the brain, including local invasive delivery, local exposure to high-intensity focused ultrasound, and permeability enhancement. These existing pharmacologic interventions have been plagued by drug failure, resistance, toxicity, and undesirable side effects, however.

In some instances, more invasive and surgical treatments are employed in treating PD, including thalamotomy, chemopallidectomy, and neurostimulation. These approaches typically require longer recovery times and intensive follow up treatments. In some cases, more invasive treatments can lead to future complications. As a result of the limitation of these previous approaches, treatment and prevention of neurodegenerative diseases has been limited.

In addition to α-synuclein deposits, neuroinflammation is another pathological feature of PD. See Wake H. et al., *Trends Neurosci,* 36: 209-17, 2013. Neuroinflammation is caused by microglia, a brain resident immune cell. Microglia could be activated by various types of stimuli resulting in neuroinflammation, including systemic inflammation, brain injury, and ischemia. Recent studies have also showed that extracellular α-synuclein can also induce activation of microglia. Exposure to various forms of recombinant α-synuclein can induce activation of microglia. Additionally, neuron-released oligomeric forms of α-synuclein induce microglia activation via interaction with TLR2 and β1-integrin on the surface of microglia.

In this regard, accumulations of reactive microglia have been found in the brains of PD patients, and elevated levels of inflammatory cytokines, such as TNFα and IL6 have been detected in the CSF and plasma of PD patients. See Hunot S. et al., *Ann Neurol* 53 Suppl. 3: S49-58, S58-60, 2003. Although there is evidence that inflammation plays a role in neurodegenerative diseases such as PD and AD, the data are often conflicting, however.

Inflammation is a very complicated process with many components and mechanisms at the molecular and cellular level. See Wyss-Coray & Mucke, *Neuron,* 35(3): 419-32, 2002. While many inflammatory responses are harmful, some specific responses may be beneficial and protective against neurodegeneration. It remains uncertain to what extent inhibiting inflammation can reduce neurodegenerative disease and simply inhibiting inflammation does not necessarily provide a therapeutic effect. For example, "no significant effects were observed on the progression of AD in treatment trials with a variety of compounds that strongly suppress inflammation, including corticosteroids, diclofenac/misoprostol, COX-2 inhibitors and hydroxychloroquine." See id.

In the case of PD, the use of nonsteroidal anti-inflammatory drug (NSAIDs), such as aspirin, can inhibit the neurodegenerative process whereas treatment with some NSAIDs can aggravate this process. NSAIDs are a heterogeneous chemical group with different potency in crossing the blood-brain barrier and this might explain the differences among the studies and the sometimes conflicting results. For prevention of disease onset, use of NSAIDs was associated with a 20% reduction in the incidence of PD in men, but a 20% increase in the incidence of PD among women. See Esposito et al., *Experimental Neurology,* 205: 295-312, 2007. Therefore, as indicated in the conclusion section of this review paper, "further clarification of the role of inflammation in the pathophysiology of basal ganglia disorders is required, since the overall picture is still confusing. Complicating the situation is the fact that inflammation is a 'double-edged sword' and probably starts as a beneficial defense mechanism that at some point evolves into a destructive and uncontrollable chronic reaction. Thus, the ideal approach would be to inhibit the deleterious effects associated with neuroinflammation while preserving the inflammatory pathways that lead to neuroprotection." See id.

SUMMARY OF THE INVENTION

The following discloses a simplified summary of the specification in order to provide a basic understanding of some aspects of the specification. This summary is not an extensive overview of the specification. It is intended to neither identify key or critical elements of the specification nor delineate the scope of the specification. Its sole purpose is to disclose some concepts of the specification in a simplified form as a prelude to the more detailed description that is disclosed later.

The present invention aims to overcome the drawbacks of the existing treatments and medicaments used in the treatment of various neurodegenerative diseases by proposing a medicament that obviates the need for surgical intervention. The present invention provides a description of novel compounds which penetrate the blood-brain barrier and methods of treating a host, such as a human, suffering from PD or other neurodegenerative diseases with hypoestoxide (HE), its derivatives, and related compounds, whether in pure form or contained in the native plant source, that such pathological conditions are ameliorated thereby. It is especially noted that hypoestoxide has very low toxicity compared to other available drugs used for treating PD or other neurodegenerative diseases. The reference compound, hypoestoxide, comprises the formula (I):

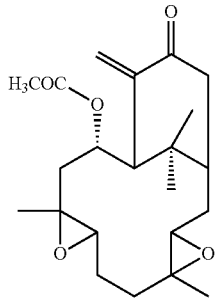

(I)

Additionally, hypoestoxide-related natural plant products comprise the formulae:

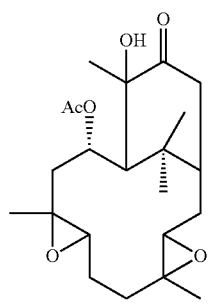

12-hydroxydihydropoestoxide (II)

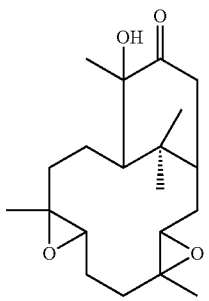

10-deacetoxy-12-hydroxydihydrohypoestoxide (III)

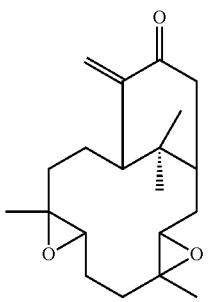

10-deacetoxyhypoestoxide (IV)

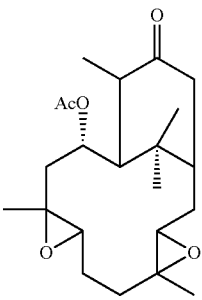

12,18-dihydrohypoestoxide (V)

An effective amount of one or a mixture of formulae I through V may be administered to an afflicted host for treating and/or ameliorating at least one symptom of neurodegenerative diseases. The compounds of the invention may also be used in combination with other therapeutic agents for the treatment and prevention of PD and other neurodegenerative diseases. The present invention further provides methods of prophylaxis and therapy to prevent the development of PD in individuals who have a positive biomarker indicating a potential to develop PD or other neurodegenerative disease over time. In this way, the present invention also aims to serve as a very important prophylactic treatment for large populations at risk.

Additional objects and advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and not to be viewed as being restrictive of the invention, as claimed.

BRIEF DESCRIPTION OF THE DRAWINGS

Certain aspects of this invention can be understood with reference to the following figures.

DETAILED DESCRIPTION OF THE INVENTION

Figure 1A:
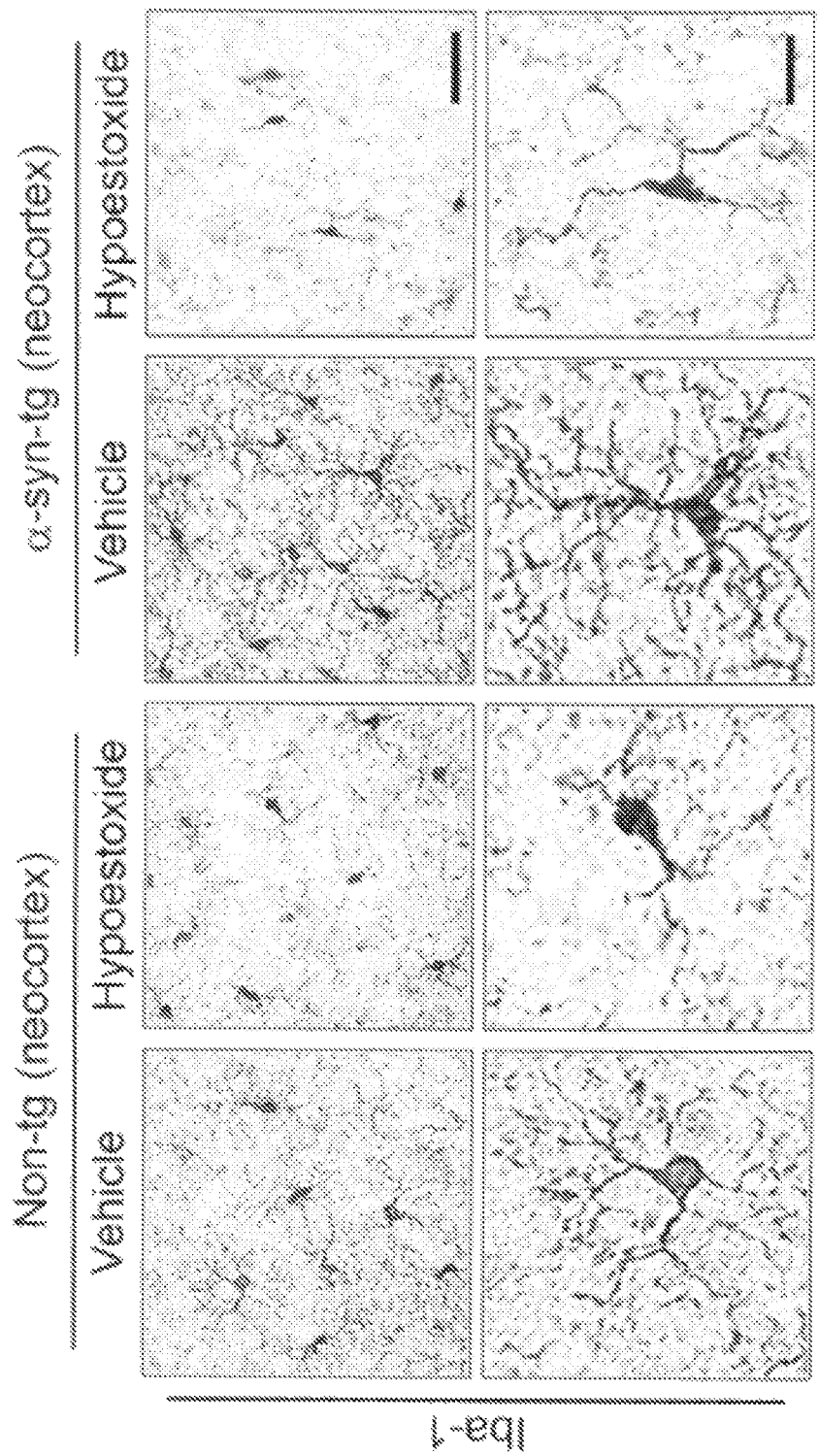
FIG. 1A through FIG. 1F show analysis of the numbers of brain immune cells in the neocortex of α-syn-tg mice.
Figure 1B:
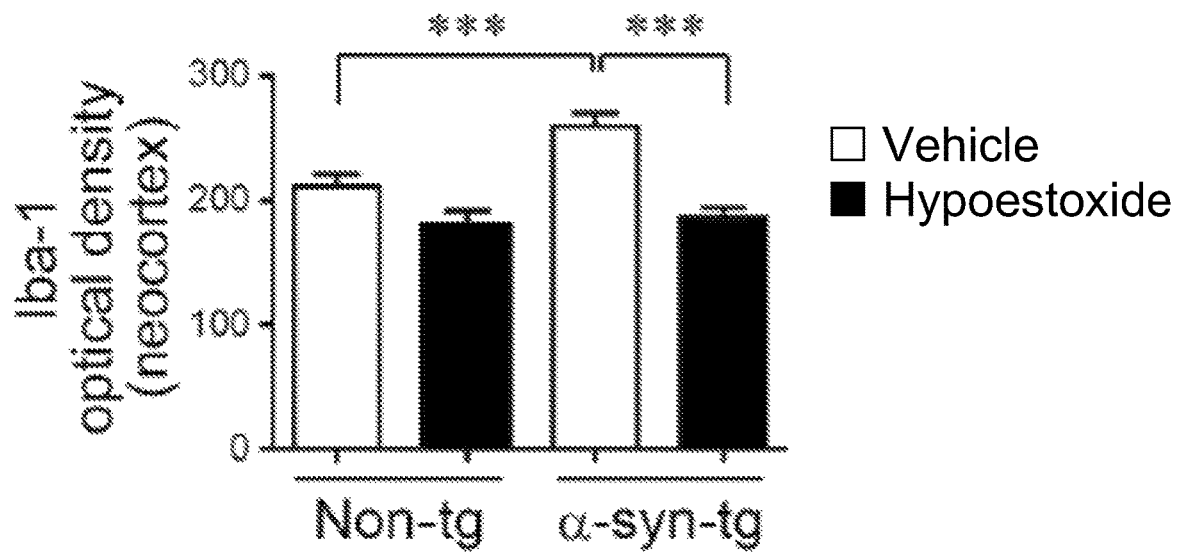
Figure 1C:
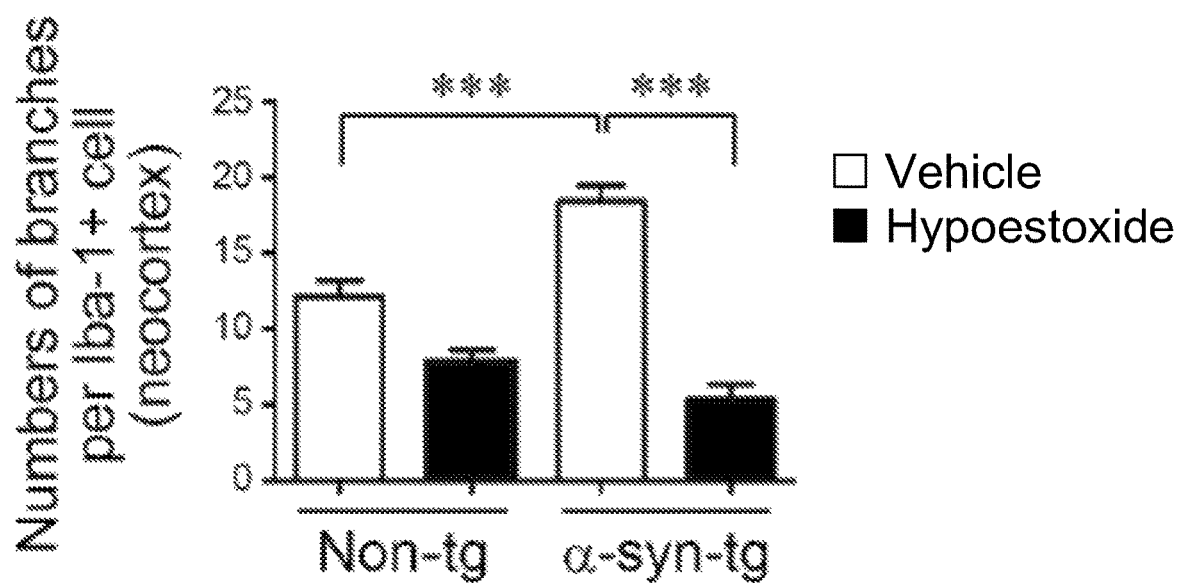
Figure 1D:
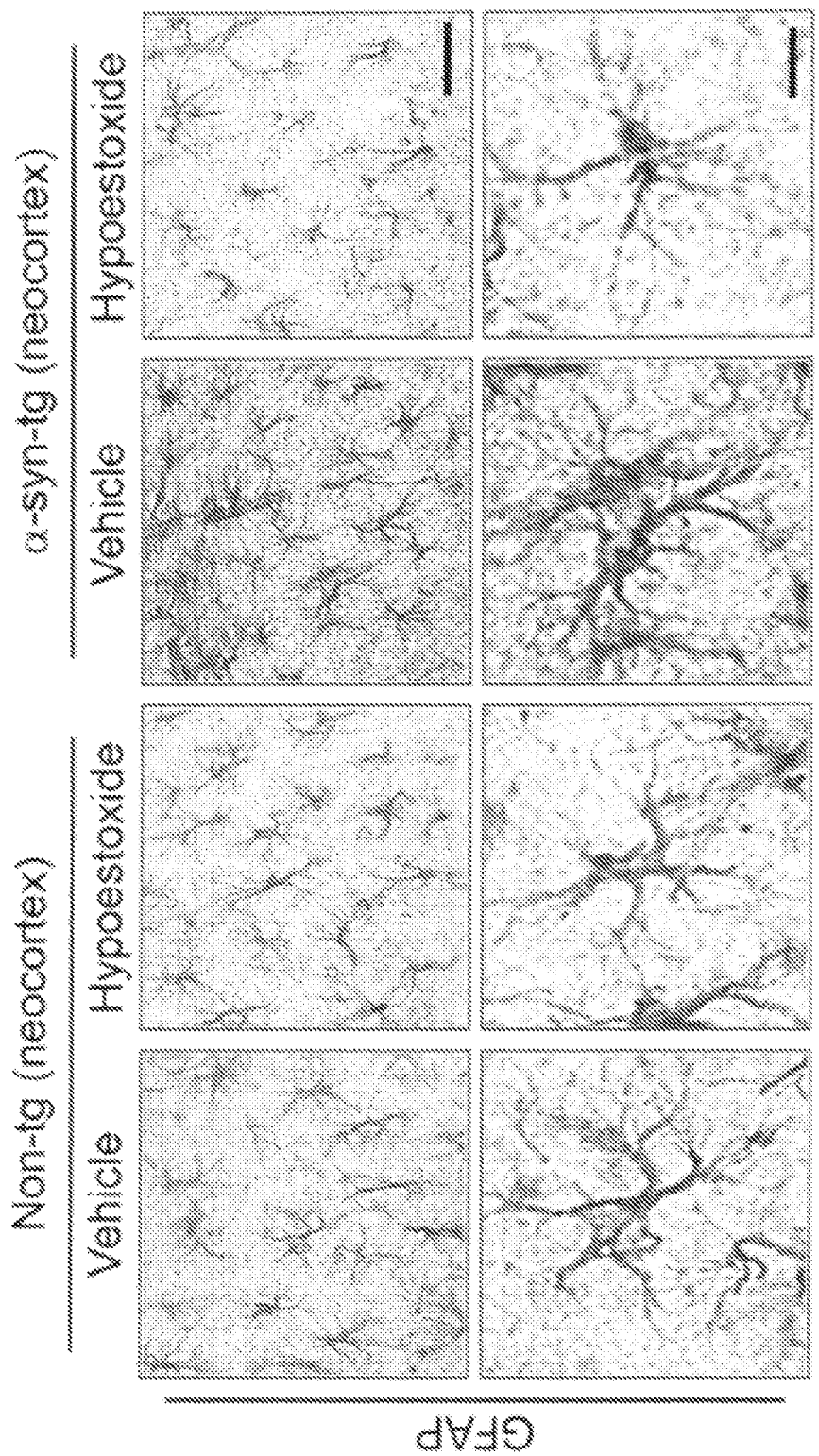
Figure 1E:
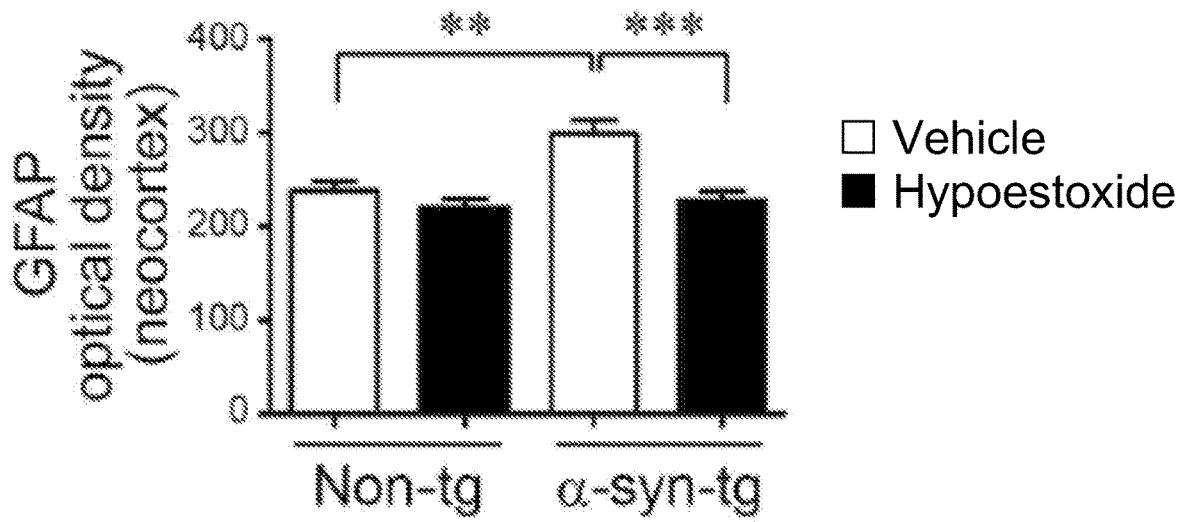
Figure 1F:
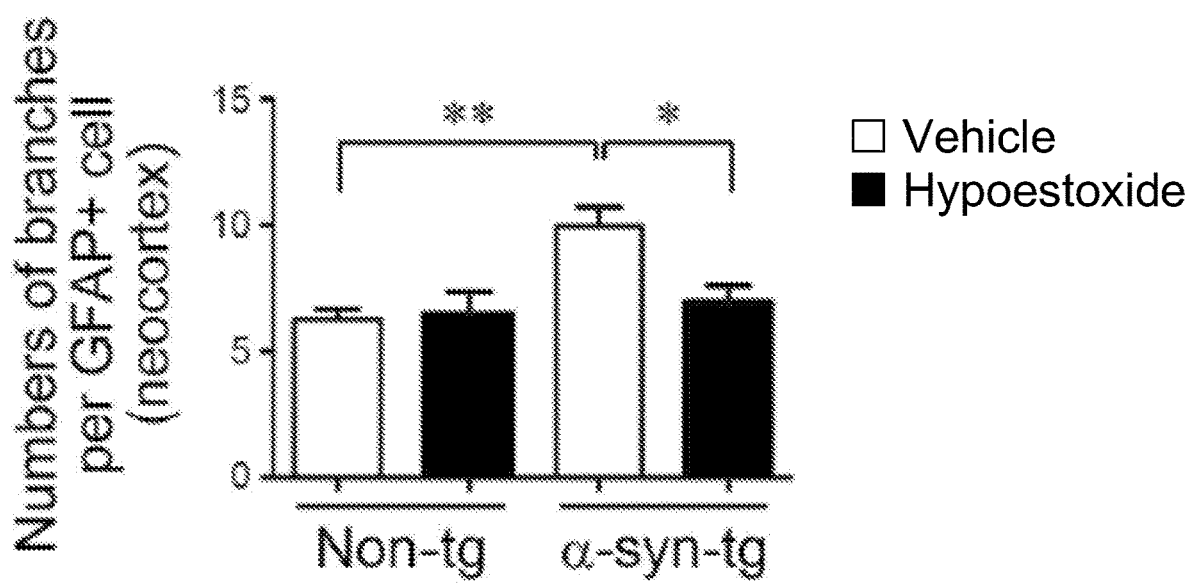

The present invention is directed towards hypoestoxide, its derivatives, and related compounds thereof and methods for treating and/or preventing neurodegenerative diseases, such as PD. Various modifications obvious to one skilled in the art are deemed to be within the spirit and scope of the present invention.

Definitions

The term "exemplary" is used herein to mean serving as an example, instance, or illustration. Any aspect or design described herein as "exemplary" is not necessarily to be construed as preferred or advantageous over other aspects. Rather, use of the word exemplary is intended to disclose concepts in a concrete fashion. As used in this application, the term "or" is intended to mean an inclusive "or" rather than an exclusive "or." Additionally, the articles "a" and "an" as used in this application and the appended claims should generally be construed to mean "one or more" or "at least one," thus including individual components as well as mixtures/combinations, unless specified otherwise or clear from context to be directed to a singular form.

The terms "manage," "managing," and "management" as used herein encompass preventing the recurrence of the specified disease or disorder in a patient who has already suffered from the disease or disorder, and/or lengthening the time that a patient who has suffered from the disease or disorder remains in remission. The terms encompass modulating the threshold, development, and/or duration of the disease or disorder, or changing the way that a patient responds to the disease or disorder.

The terms "prevent," "preventing," and "prevention" contemplate an action that occurs before a patient begins to suffer from the specified disease or disorder, which inhibits or reduces the severity of the disease or disorder. In other words, the terms encompass prophylaxis as used herein.

The terms "therapeutically effective amount" of a compound as used herein is an amount sufficient to provide a therapeutic benefit in the treatment or management of a disease or condition, or to delay or minimize one or more symptoms associated with the disease or condition. A therapeutically effective amount of a compound means an amount of a therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

The terms "treat," "treating," and "treatment" as used herein contemplate an action that occurs while a patient is suffering from the specified disease or disorder, which reduces the severity of the disease or disorder, or retards or slows the progression of the disease or disorder.

Finally, the term "include" as used herein has the same meaning as "include, but not limited to," and the term "includes," has the same meaning as "includes, but is not limited to." Similarly, the term "such as" has the same meaning as the term, "such as, but not limited to."

Compounds

In a preferred embodiment, the present invention provides a novel pharmaceutical composition, the composition comprising hypoestoxide, including mixtures or derivative of hypoestoxide derived from either natural or synthetic sources. Hypoestoxide comprises the following formula I:

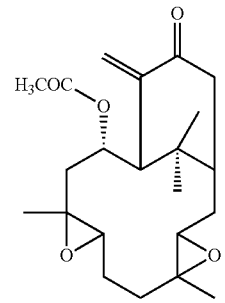

(I)

Hypoestoxide is a natural diterpene isolated from the shrub *Hypoestes rosea* (Acanthaceae). Studies have demonstrated that hypoestoxide may modulate the activity of NF-κB through IκB kinase inhibition. Thereby, hypoestoxide has been previously suggested as a potential anti-inflammatory and anti-cancer drug. The polar surface area for hypoestoxide is 68.4 square angstroms, which is considered very good for blood brain barrier penetration to deliver therapeutic drugs. Therefore, the potency of hypoestoxide as an anti-neuroinflammatory drug for PD has been examined using a mouse model. In this regard, administration of hypoestoxide ameliorates neuroinflammation, neurodegeneration, and behavioral defects in a PD mouse model via modulation of NF-κB activity.

Other embodiments of the present invention encompass compounds of the following formulae II-V:

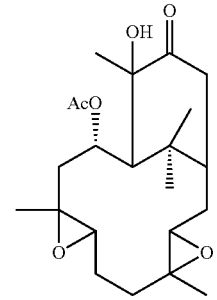

(II)

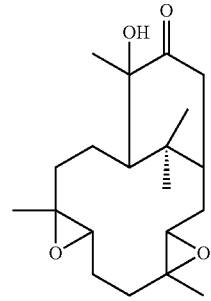

(III)

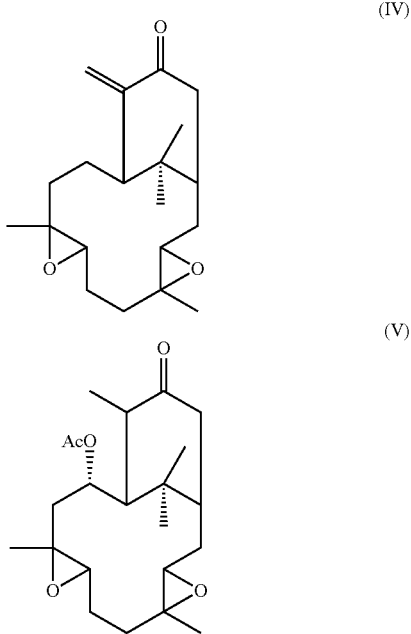

Formula II through formula V are described and have been characterized by standard chemical methods known in the art, such as ultraviolet spectrophotometry, mass spectrometry, nuclear magnetic resonance spectroscopy, and the like. Formulae II through IV are isolated from the extract of the shrub *Hypoestes rosea* while formula V is prepared from pure hypoestoxide by catalytic hydrogenation using a palladium catalyst. This reaction is illustrated in the equation below:

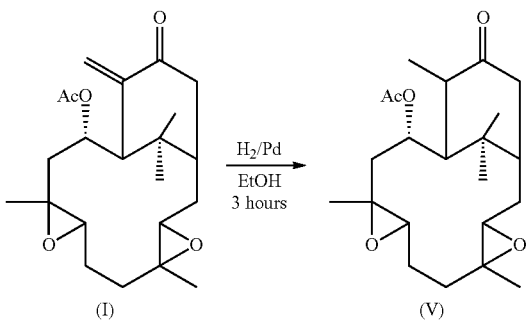

Methods of Use

The embodiments of the present invention provide compositions (i.e., formulae I through V) for treating and/or preventing neurodegenerative diseases in a host (e.g., an animal or human). Another embodiment of the present invention provides a method of prevention and/or treatment of neurodegenerative diseases in a host. The method includes administration of an effective amount of an agent having a formula selected from the group consisting of formulae I through V, and mixtures thereof such that at least one condition or symptom related to or associated with the neurodegenerative disease is treated or at least partially alleviated. Preferably, treatment should continue as long as symptoms are suspected or observed. In one embodiment, the present method prevents and/or treats PD. It is also contemplated that hypoestoxide, one or more of its derivatives, related natural plant products, or a combination thereof, may also be used to treat or prevent other neurodegenerative diseases, such as, but not limited to AD, Lewy body dementia, Huntington's disease, MS, and multiple system atrophy, among others.

Another embodiment encompasses a method of reducing the numbers of microglial cells and the levels of astrogliosis in the neocortex in a patient, which comprises administering to the patient an effective amount of a compound of the present invention.

Another embodiment encompasses a method of reducing the production of pro-inflammatory cytokines in a patient, which comprises administering to the patient an effective amount of a compound of the present invention.

Another embodiment encompasses a method of decreasing the loss of TH-positive striatal fibers in a patient, which comprises administering to the patient an effective amount of a compound of the present invention.

Another embodiment encompasses a method of decreasing the levels of α-synuclein in neurons and neuropil in a patient, which comprises administering to the patient an effective amount of a compound of the present invention.

Another embodiment encompasses a method of decreasing the levels of SDS-insoluble α-synuclein in a patient, which comprises administering to the patient an effective amount of a compound of the present invention.

Another embodiment encompasses a method of reducing the level of phosphorylated NF-κB in a patient, which comprises administering to the patient an effective amount of a compound of the present invention.

The amount, route of administration, and dosing schedule of a compound will depend upon various factors such as the specific indication to be treated, prevented, or managed, the type of the disease, the progression of the disease, other therapy used, and the age, sex, and condition of the patient. The roles played by such factors are well known in the art, and may be accommodated by routine experimentation. In a particular embodiment, a compound of the invention is administered to a human patient in an amount of about 0.1, 0.5, 1.0, 3.0, 5.0, 10.0, 15.0, to about 200 mg/kg/day of hypoestoxide, hypoestoxide derivative, a related compound, or a combination thereof from about 0.1 mg to 200 mg/kg/day.

Pharmaceutical Formulations

The present pharmaceutical composition comprising one or more compounds of the invention for treating and/or preventing PD can be provided in any and all dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Accordingly, pharmaceutical or pharmacological compositions of the present invention may be prepared as an injectable, either as liquid solutions or suspensions; or solid forms, suitable for solution in, or suspension in, liquid prior to injection.

Other examples of dosage forms include, but are not limited to tablets, fine granules, wafers, capsules (including time release capsules), cachets, troches, lozenges, dispersions, suppositories, ointments, cataplasms, pastes, powders, dressings, creams, plasters, solutions, patches, aerosols, gels, elixirs, syrups, and others. Preferred forms are tablets, including chewable tablets. The dosage unit forms will generally contain between from about 0.1, 0.5, 1.0, 3.0, 5.0, 10.0, 15.0, to about 200 mg/kg/day of hypoestoxide, hypoestoxide derivative, a related compound, or a combination thereof from about 0.1 mg to 200 mg/kg/day.

In this regard, the formulation should suit the mode of administration. For instance, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and deliver across cell membranes to intracellular sites.

Additionally, the pharmaceutical composition of the present invention for treating and/or preventing PD may be manufactured using an excipient, binder, disintegrator, lubricant, and/or other formulation additives. The composition may be provided in sustained release dosage forms. The dosage forms may be manufactured by coating the tablets, granules, fine granules, and/or capsules with oleaginous substances. Non-limiting examples of oleaginous substances include triglycerides, polyglycerol fatty acid esters and hydroxypropylcellulose.

The exact magnitude of a prophylactic or therapeutic dose will vary with the type of the disease, the progression of the disease, other therapy used, and the route of administration, among other factors. For instance, in cases where the disease has already progressed into later stages and is more aggressive, a larger dose of the compounds may be needed. Additionally, the dosage form may be administered once or twice daily, with, or without food. Higher dosages may be administered if the dosage form is administered less frequently.

Preferably, dosage should be low at the beginning of the therapy and increased in increments depending on the patient's response. Additionally, infants, children, and elderly patients, as well as patients with impaired renal or hepatic function or other impairments should initially receive lower doses, and that they be titrated based on global response and blood level. It may be necessary to use dosages outside of these ranges in some cases. Further, it is noted that the clinician or treating physician will know how and when to interrupt, adjust, or terminate therapy in conjunction with individual patient response. For instance, the therapeutic dose may be reduced when the condition or symptom is ameliorated.

Examples

Aspects of this invention can be understood from the following examples, which do not limit its scope.

Animal Treatment and Behavioral Analysis

Five-month-old non-tg and α-syn-tg female mice were injected intra-peritoneally (IP) with either vehicle (40% captisol) or 5 mg/kg of hypoestoxide daily for four weeks. The right hemibrains were post-fixed in phosphate-buffered 4% PFA at 4° C. for neuropathological analysis, while the left hemibrains were snap-frozen and stored at −70° C. for subsequent protein and mRNA analysis.

Following treatment, the mice were assessed for gait and coordination using the open field and the round beam tests. Total activity was calculated as total beam breaks in ten minutes. The impairment of gait and balance were assessed by round beam analysis. Three consecutive trials of one minute each were run in one day. The numbers of foot slippages and distance traveled were recorded. The total errors on the beam were calculated as foot slips/distance traveled.

Immunohistochemistry and Immunofluorescence and Neuropathological Analysis

Blind-coded sagittal brain sections were incubated with primary antibodies at 4° C. for overnight. The next day, sections were incubated with either biotinylated- or FITC-conjugated secondary antibodies and detected with avid in D-HRP HRP (ABC elite, Vector Laboratories, Burlingame, Calif.) and with Tyramide Signal Amplification Direct system (PerkinElmer, Waltham, Mass.), respectively.

To determine the neuroinflammation, neurodegeneration, accumulation of α-synuclein, and NF-κB activation, brain sections were stained with Iba-1, GFAP, TNFα, IL-1β, IL6, human α-synuclein, NF-κB, and phosphorylated-NF-κB antibodies, respectively. Sections were imaged by Olympus BX41 microscope. All immunoreactivity levels were determined by optical density analysis using Image Quant 1.43 program (NIH) except the immunoreactivity of Iba-1. The cell numbers of Iba-1-positive cells were determined per field (230 µm×184 µm) of each animal based on cell body recognition using Image Quant 1.43 program (NIH).

Preparation of Tissue Extract and Western Blot Analysis

Brain homogenates were prepared in the lysis buffer to separate SDS-soluble and SDS-insoluble fractions. Chemiluminescence detection and analysis were performed using Versadoc XL imaging apparatus and Quantity One (Bio-rad, Hercules, Calif.).

Quantitative Polymerase Chain Reaction (qPCR)

Total mRNA was extracted from mice frontal cortex using RNeasy Lipid mini kit (Qiagen, Germantown, Md.) and reverse transcribed using SuperScript VILO cDNA synthesis kit (Life Technologies), respectively. Quantitative real-time PCR was performed using TaqMan® Fast Advanced Master Mix (Life Technologies) according to manufacturer's instructions with gene specific primers obtained from Life Technologies, such as TNFα (Mm00443258_m1), IL6 (Mm00446190_m1), IL-1β (Mm00434228_m1), and β-actin (Mm00607939_s1). Amplification of DNA products was measured by the StepOnePlus real-time PCR system (Applied Biosystems, Carlsbad, Calif.). Relative mRNA levels were calculated according to the 2-exp (ΔΔCt) method. All ΔCT values were normalized to β-actin.

Measuring Effects on Neuroinflammation in a Mouse Model of PD

FIGS. 1A-1F show analysis of the numbers of brain immune cells. Iba-1-positive microglia and GFAP-positive astrocytes were significantly increased in the neocortex of α-syn-tg mice. FIGS. 1A-1B and 1D-1E also show that administration of HE significantly decreased the numbers of microglial cells and the levels of astrogliosis in the neocortex in α-syn-tg mice to levels similar to those in non-tg mice.

In addition to a decrease in overall numbers of immune cells in the α-syn-tg mice, FIGS. 1A, 1C, 1D, and 1F show that the numbers of branches per glial cell decreased. A positive interactive effect of HE treatment on Iba-1 optical density ($F_{interaction\ (1,\ 16)}$=80.48, p<0.0001), numbers of microglia branches ($F_{interaction\ (1,\ 16)}$=83.25, p<0.0001), GFAP optical density ($F_{interaction\ (1,\ 16)}$=15.88, p=0.0011), and numbers of astroglial branches ($F_{interaction\ (1,\ 16)}$=4.04, p=0.0616) was confirmed by two-way ANOVA.

The levels of pro-inflammatory cytokines were analyzed using immunohistochemical analysis and gene expression analysis. The levels of TNFα, IL-1ß and IL6 were increased in α-syn-tg mice compared to non-tg mice. In contrast, treatment of HE significantly reduced the levels of these pro-inflammatory cytokines in the neocortex of α-syn-tg mice. A positive interactive effect of HE treatment on the levels of TNFα ($F_{interaction\ (1,\ 16)}$=12.34, p=0.0029), IL-1β ($F_{interaction\ (1,\ 16)}$=11.58, p=0.0036), and IL6 ($F_{interaction\ (1,\ 16)}$=31.06, p<0.0001) was confirmed by two-way ANOVA.

In addition, quantitative gene expression analysis showed the mRNA levels of TNFα, IL-1β and IL6 were clearly decreased by HE administration in the neocortex of α-syn-tg mice. A positive interactive effect of HE treatment on the mRNA levels of TNFα ($F_{interaction\ (1,\ 16)}$=15.78, p=0.0019), IL-1β ($F_{interaction\ (1,\ 16)}$=11.65, p=0.0051), and IL6 ($F_{interaction\ (1,\ 16)}$=6.40, p=0.0264) was confirmed by two-way ANOVA. Together, these results suggest that administration of HE inhibits activation of microglia and astrocytes, thereby reducing the production of pro-inflammatory cytokines in a mouse model of PD.

Amelioration of Neurodegeneration and Behavioral Defect by HE Administration in a Mouse Model of PD.

Figure 2A:
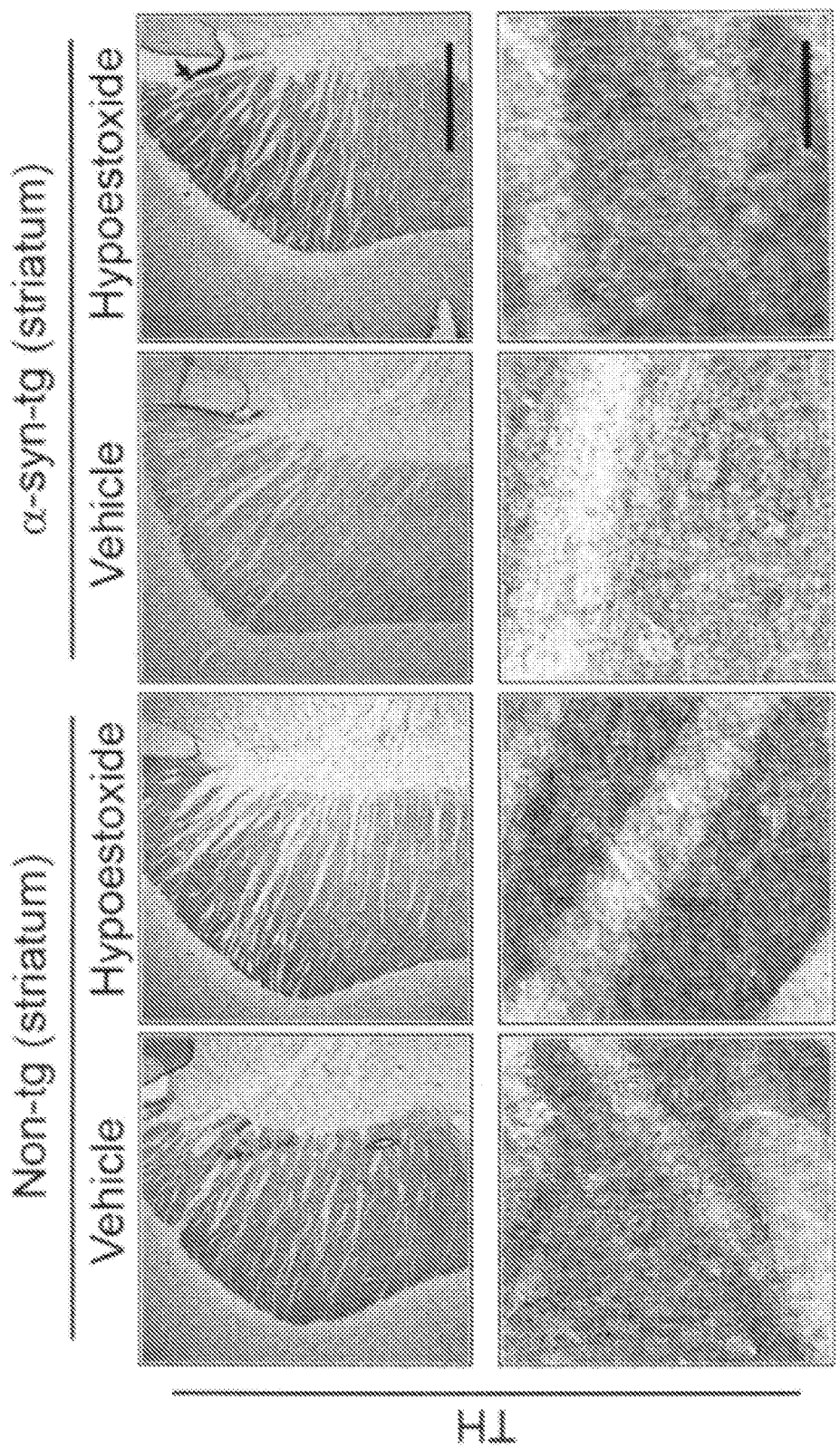
FIG. 2A through FIG. 2E show the results of neurodegeneration analysis and behavioral tests using non-tg and α-syn-tg mice treated with either vehicle or HE.
Figure 2B:
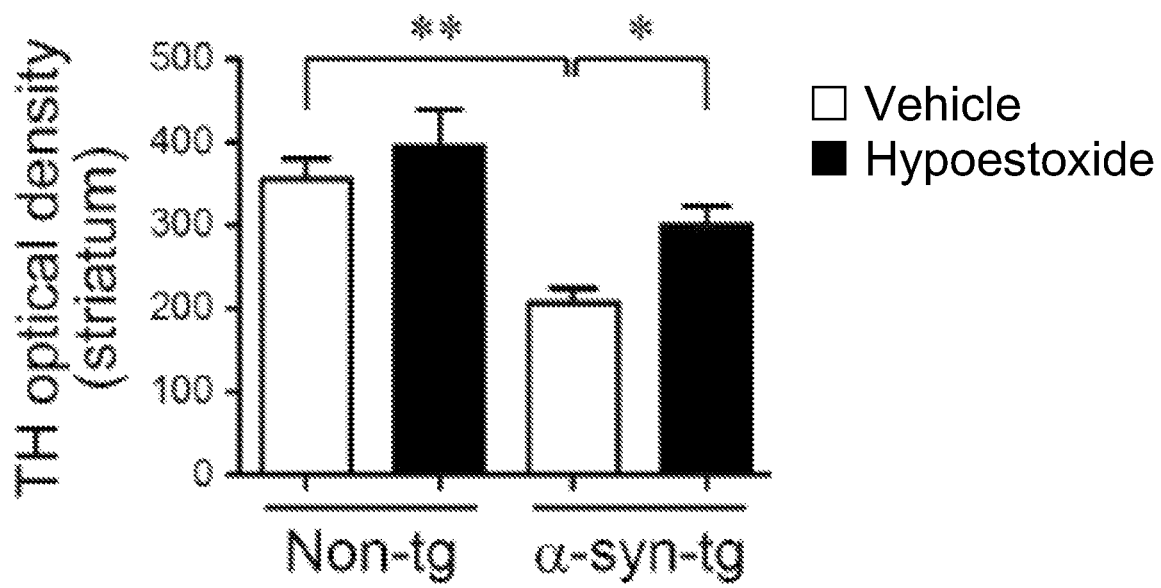
Figure 2C:
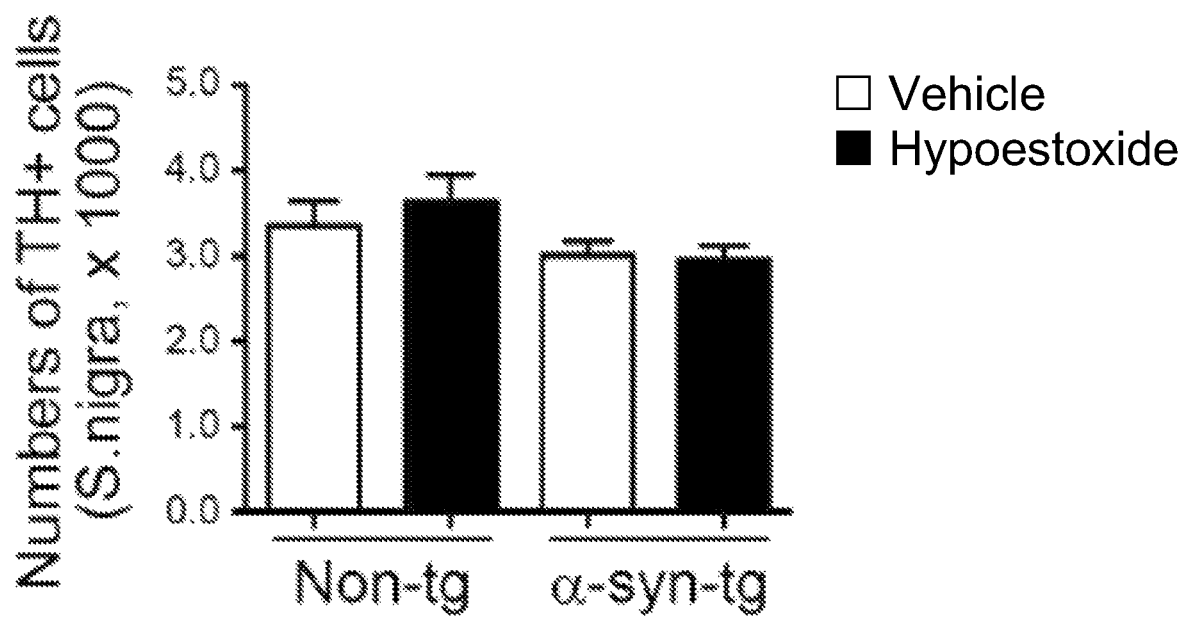

Neurodegeneration analysis and behavioral tests were performed using non-tg and α-syn-tg mice treated with either vehicle or HE. FIGS. 2A-2C show that neuronal overexpression of human α-synuclein resulted in the loss of TH-positive striatal fibers in α-syn-tg mice while the numbers of nigral TH-positive cells were not altered by α-synuclein expression. However, FIGS. 2A-2B show that administration of HE significantly decreased the loss of TH-positive striatal fibers in α-syn-tg mice. A positive interactive effect of HE treatment on the level of TH-positive striatal fibers ($F_{interaction\ (1,\ 16)}$=5.12, p=0.038) was confirmed by two-way ANOVA.

Figure 2D:
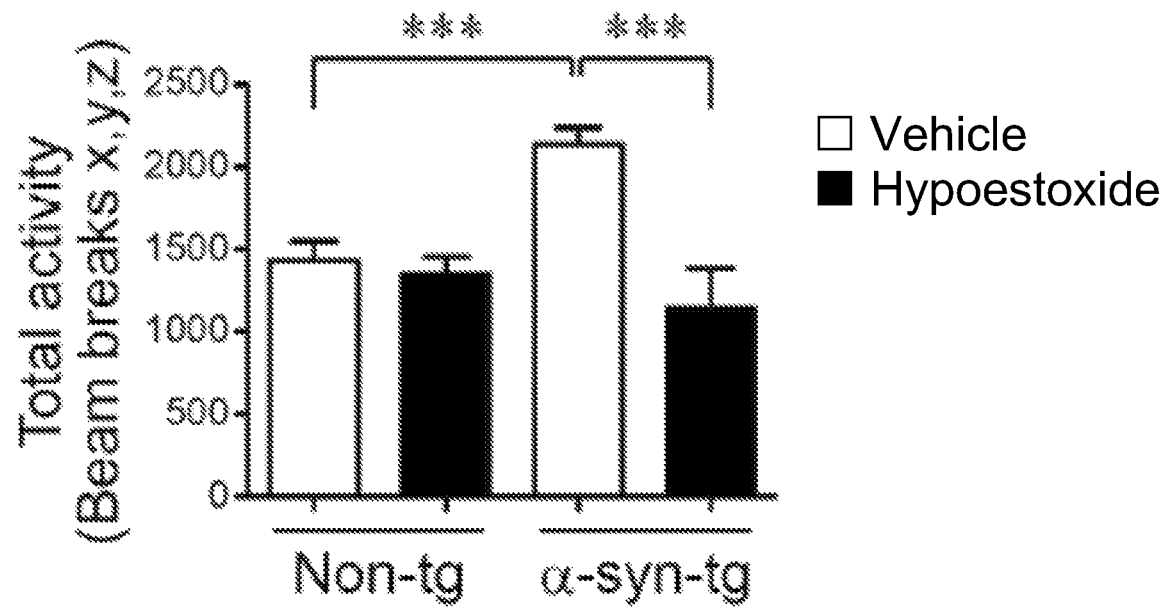
Figure 2E:
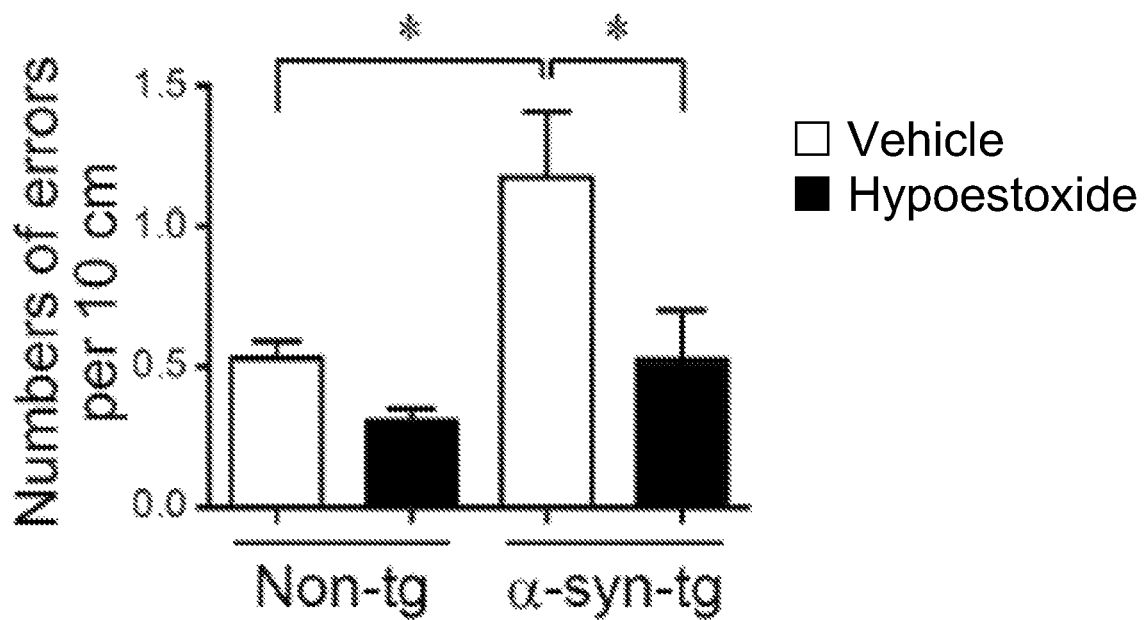

Referring now to FIGS. 2D-2E, there are shown the results of the open field and round beam tests performed to investigate the effect of HE on the anxiety-like behavior and motor behavior deficit in α-syn-tg mice. α-syn-tg mice showed a significant increase of the beam break numbers and the total round beam errors compared to non-tg control mice. Treatment of α-syn-tg mice with HE reduced these errors to levels observed in non-tg mice. A positive interactive effect of HE treatment on the beam break numbers ($F_{interaction\ (1,\ 16)}$=15.61, p=0.0011) and total round beam errors ($F_{interaction\ (1,\ 16)}$=8.58, p=0.0098) was confirmed by two-way ANOVA. Taken together, these results suggest that administration of HE prevents neurodegeneration and ameliorates behavioral defect in a mouse model of PD.

Measuring Effects on Neuronal α-Synuclein Accumulation in a Mouse Model of PD

To determine whether the behavioral improvements observed in the α-syn-tg mice were related to alterations of α-synuclein pathology, immunohistochemical analysis was performed for α-synuclein with brain sections from non-tg and α-syn-tg mice treated with either vehicle or HE. Immunohistochemical analysis showed overexpression of α-synuclein in neurons and the neuropil of α-syn-tg mice, as depicted in FIGS. 3A-3E. Administration of HE significantly decreased the levels of α-synuclein in neurons and neuropil in α-syn-tg mice. A positive interactive effect of HE treatment on the optical density of α-synuclein (frontal cortex, $F_{interaction\ (1,\ 16)}$=30.74, p<0.0001; hippocampus, $F_{interaction\ (1,\ 16)}$=13.66, p=0.0020; striatum, $F_{interaction\ (1,\ 16)}$=7.19, p=0.0164) was confirmed by two-way ANOVA.

Immunofluorescence analysis was performed with human α-synuclein specific antibodies to confirm this analysis. In this regard, mice brain sections were immunostained against human α-synuclein (Syn211 antibody) or C-terminal of human α-synuclein (Syn105 antibody).

Immunofluorescence analysis of human α-synuclein in the frontal cortex of non-tg and α-syn-tg mice treated with either vehicle or hypoestoxide was performed. (n=5 per group; unpaired t-test; *p<0.05). Error bars represent ±SEM. Additionally, fluorescence intensity against human α-synuclein was analyzed in frontal cortex of the brains. Immunoreactivity against human α-synuclein was not detected in the frontal cortex of non-tg mice, but it was highly detected in the frontal cortex of α-syn-tg mice. Similar to results from the immunohistochemical analysis, the level of human α-synuclein immunoreactivity was significantly decreased by HE administration in the frontal cortex of α-syn-tg mice.

Recent evidence suggests the C-terminal fragments of α-synuclein are particularly neuro-toxic. To determine if administration of HE affected the accumulation of these C-terminal fragments, an antibody that specifically recognizes the C-terminus of human α-synuclein was used. In this regard, immunohistochemical analysis of C-terminal of human α-synuclein in the frontal cortex of non-tg and α-syn-tg mice was performed. Additionally, optical density analysis for C-terminal of α-synuclein in frontal cortex. (n=5 per group; unpaired t-test; **p<0.01). Error bars represent ±SEM. Scale bars=250 μm (low magnification) and 25 μm (high magnification). Immunoreactivity against C-terminus human α-synuclein was also significantly decreased by HE administration in the frontal cortex of α-syn-tg mice.

Figure 3A:
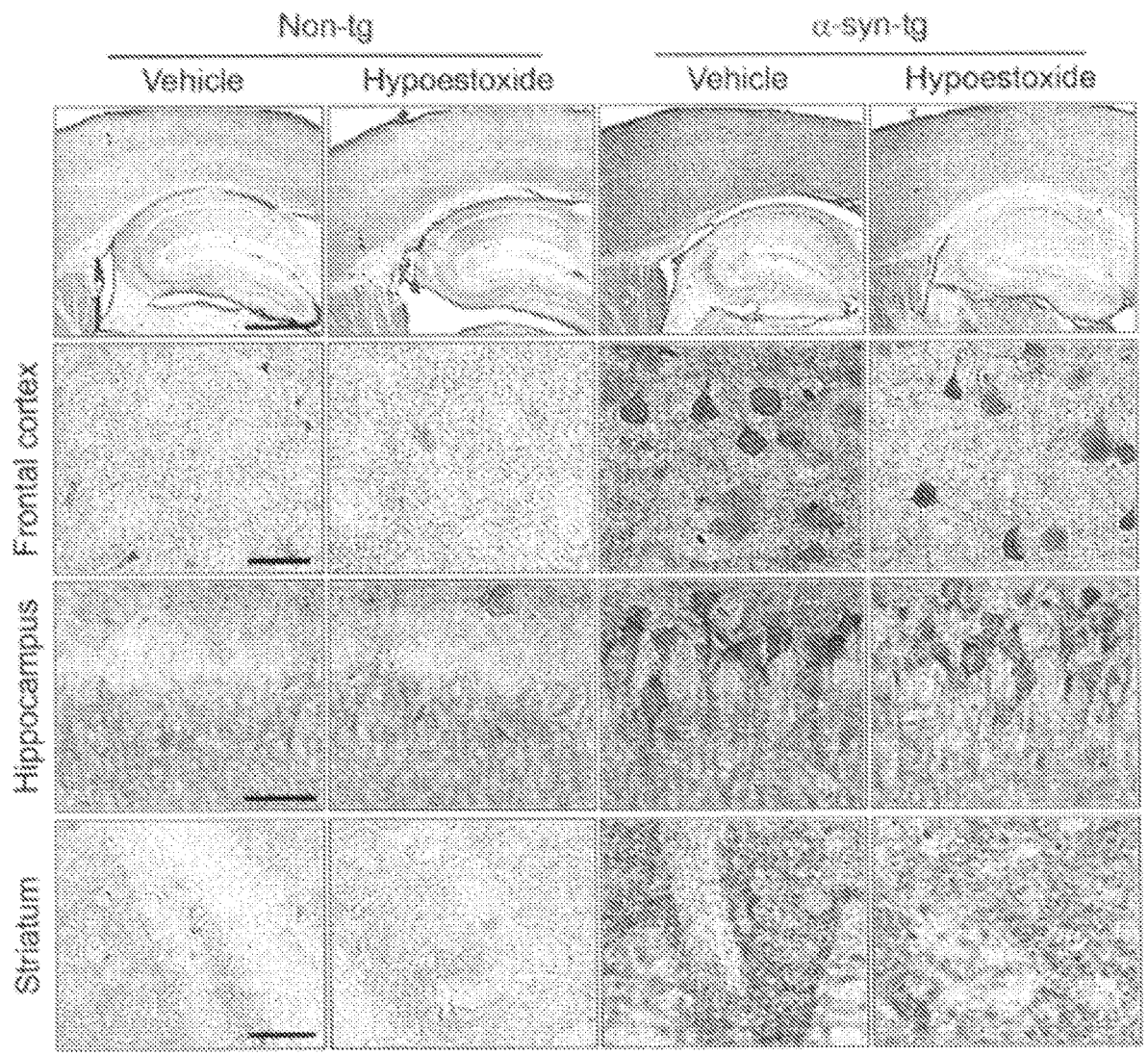
FIG. 3A through FIG. 3E show decrease of the levels of α-synuclein in neurons and neuropil in α-syn-tg mice post administration of HE.
Figure 3B:
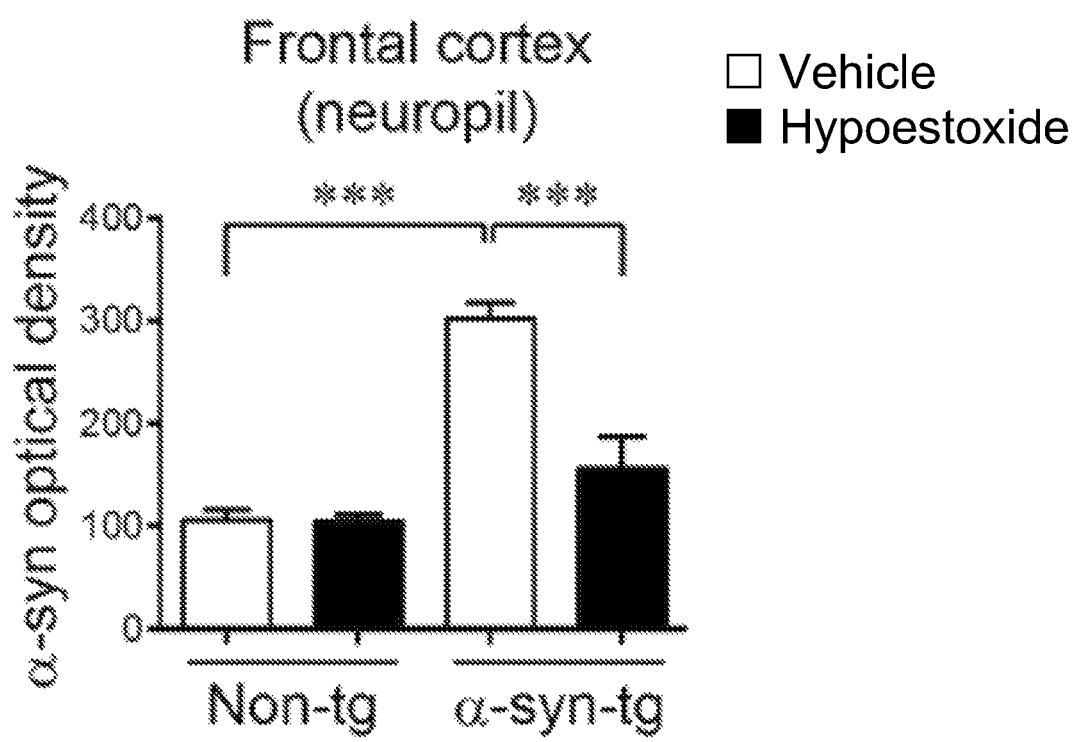
Figure 3C:
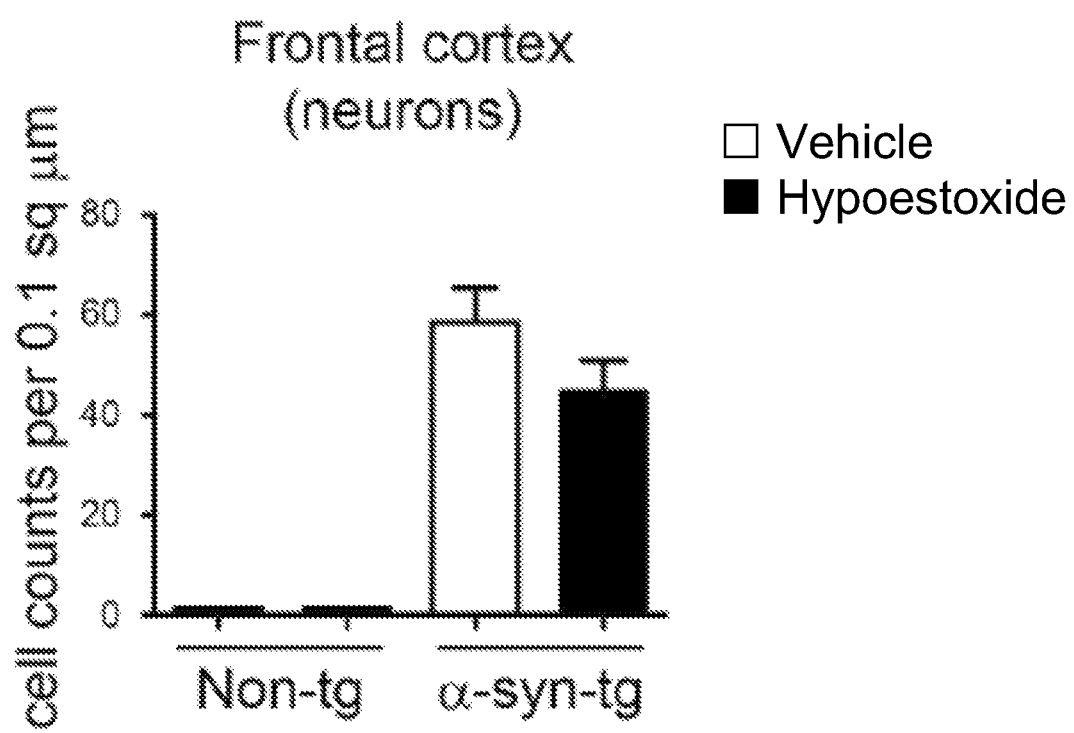
Figure 3D:
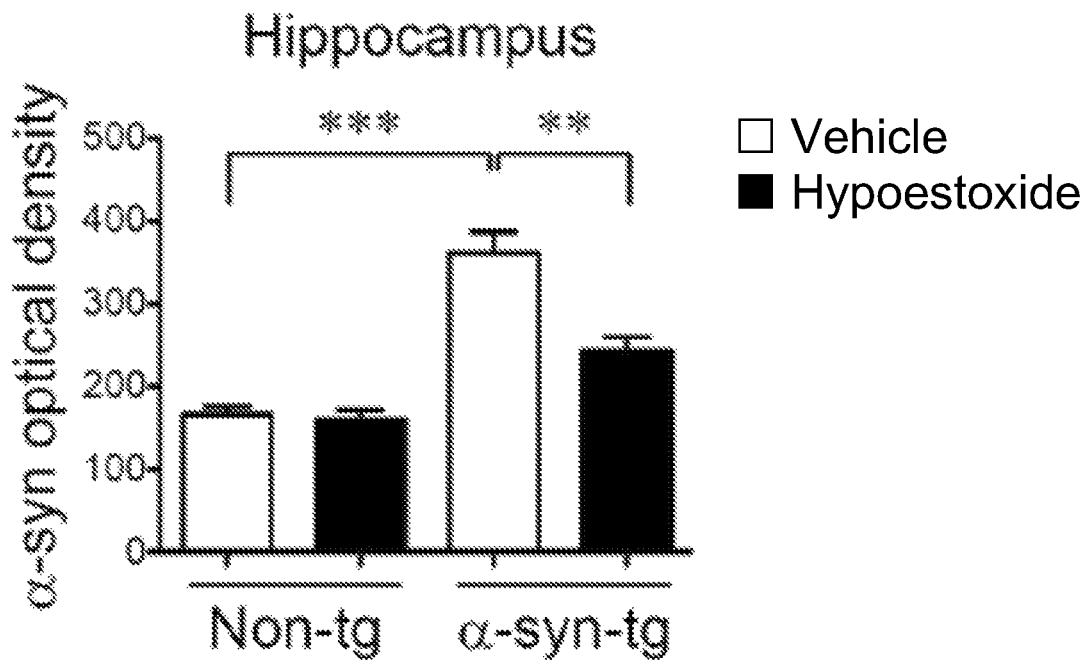
Figure 3E:
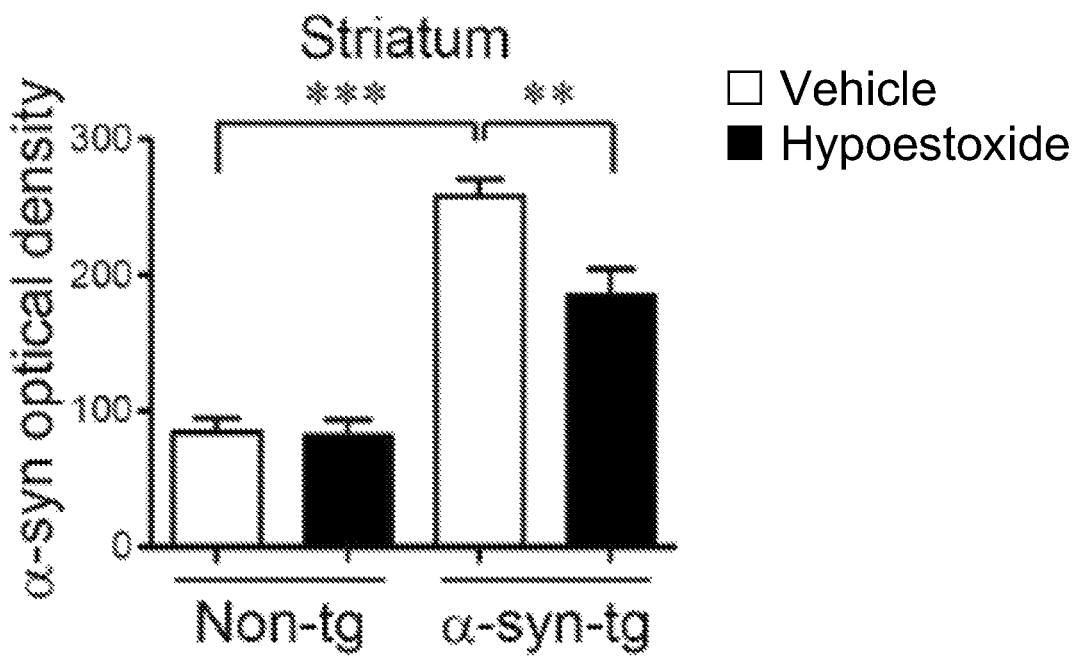
Figure 3F:
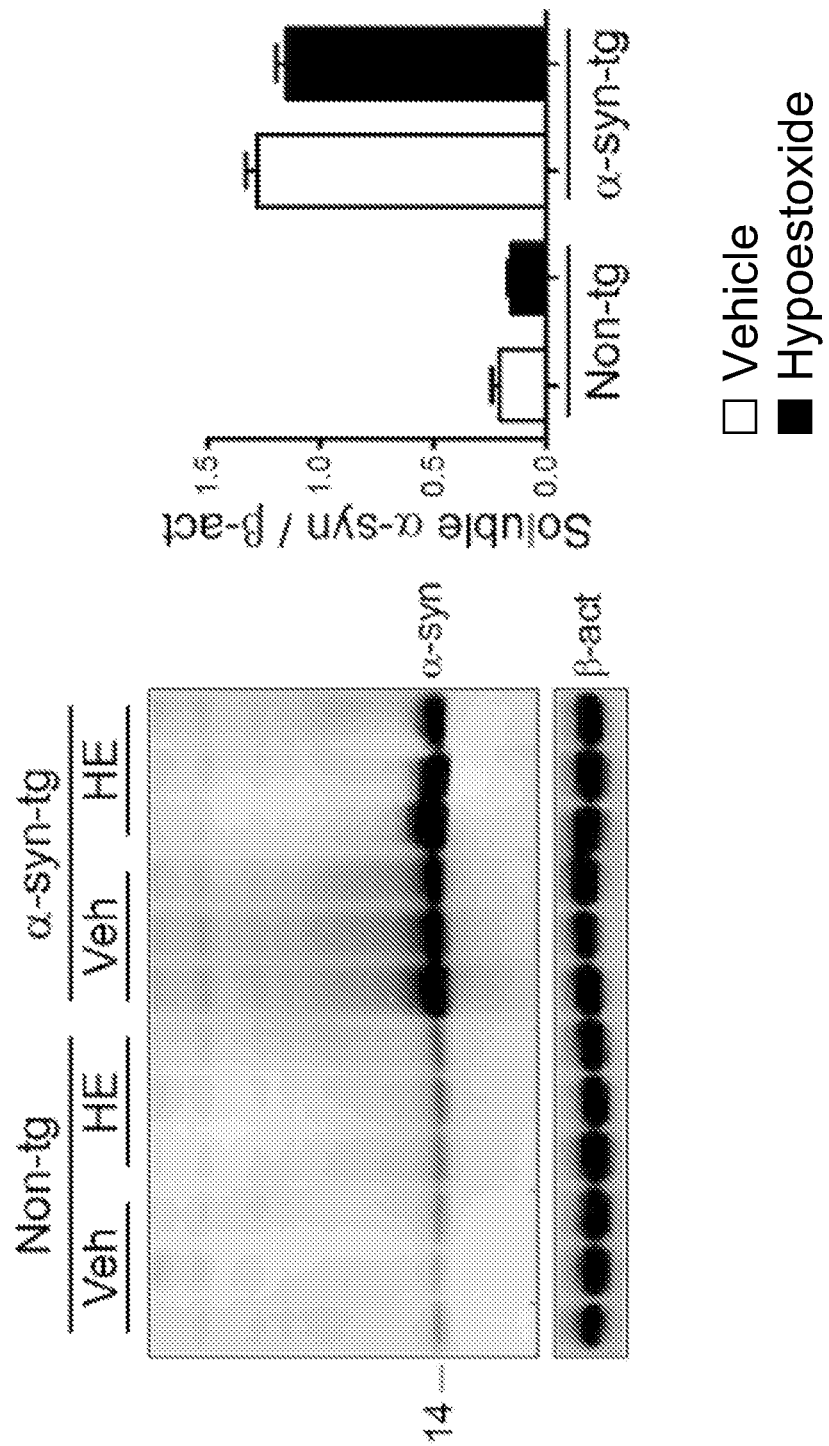
FIG. 3F and FIG. 3G show results of biochemical analysis verifying that administration of hypoestoxide reduces the accumulation of α-synuclein in a mouse model of PD.
Figure 3G:
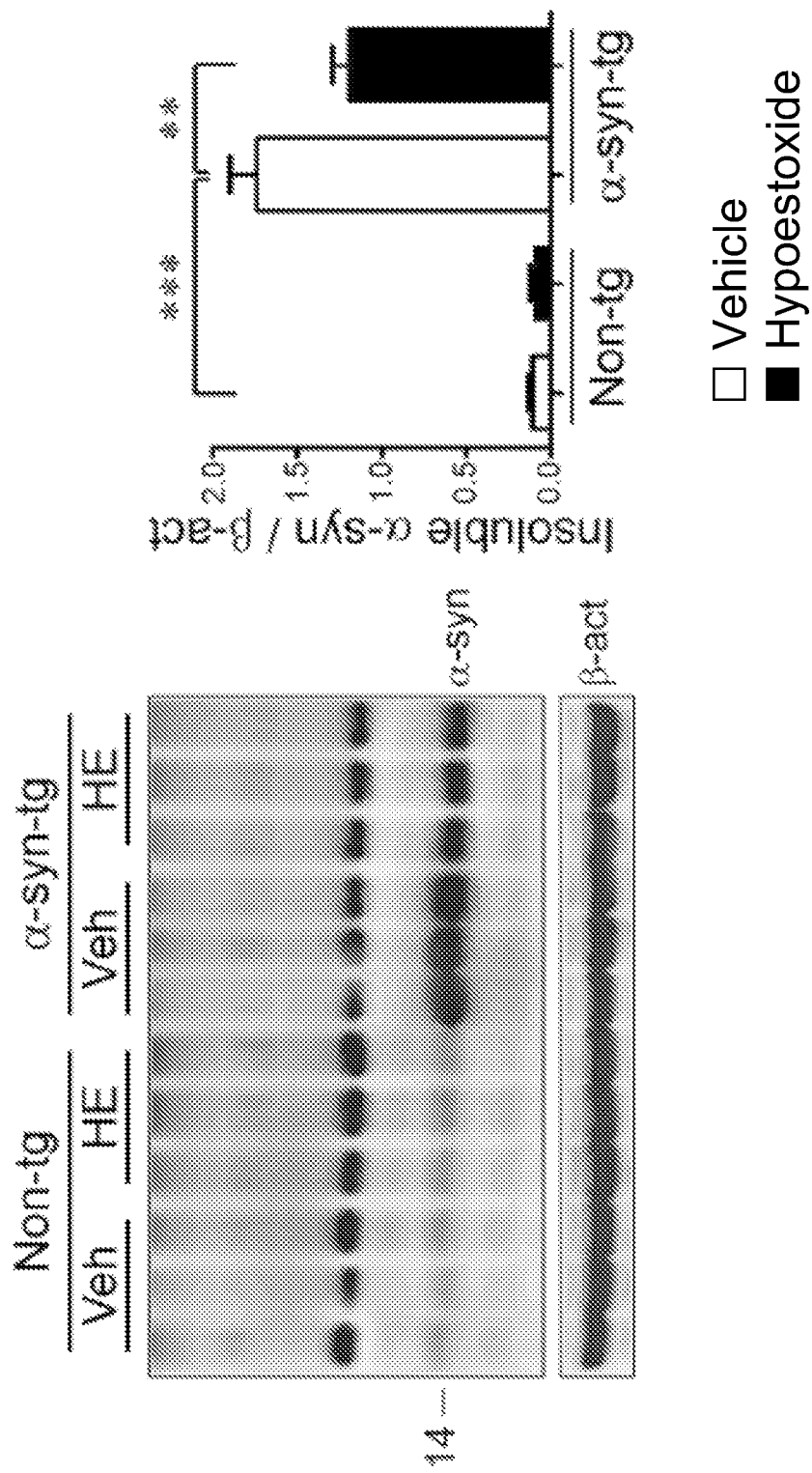

FIGS. 3F-3G show the results of a biochemical analysis. Brain homogenates were separated into SDS-soluble and SDS-insoluble factions, and analyzed by immunoblot analysis. The levels of α-synuclein in SDS-soluble fractions from α-syn tg mice were not affected by HE administration. However, the levels of SDS-insoluble α-synuclein were significantly decreased in the brain homogenates from HE-administered α-syn-tg mice. A positive interactive effect of HE treatment on the level of SDS-insoluble α-synuclein ($F_{interaction\ (1,\ 16)}$=8.68, p=0.0095) was confirmed by two-way ANOVA. Taken together, these results suggest that administration of HE reduces the accumulation of α-synuclein in a mouse model of PD.

Inhibition of NF-κB Activity in a Mouse Model of PD

Previous work suggests that HE modulated the activity of NF-κB, a key immune response signaling mediator, through inhibition of IκB kinase in immune cells. Thus, the alteration of NF-κB activity in the neocortex of non-tg and α-syn-tg mice that received either vehicle or HE was investigated. Immunofluorescence analysis showed that total levels of NF-κB were not changed by HE administration in the neocortex of non-tg or α-syn-tg mice. However, the level of immunoreactivity against phosphorylated-NF-κB, the activated form of NF-κB, was highly elevated (by four-fold) in the neocortex of α-syn-tg mice. In addition, the elevated level of phosphorylated-NF-κB was significantly decreased by administration of HE in the neocortex of α-syn-tg mice to levels observed in non-tg mice. A positive interactive effect of HE treatment on the immunoreactivity of phosphorylated-NF-κB ($F_{interaction\ (1,\ 16)}$=27.70, p<0.0001) was confirmed by two-way ANOVA.

Biochemical analysis using brain homogenates from the cortex of non-tg and α-syn-tg mice was performed. Brain homogenates were separated into cytosolic and nuclear fractions by centrifugation, and each fraction was analyzed by western blot analysis. Total levels of NF-κB were not altered by HE administration in non-tg and α-syn-tg mice. However, the level of phosphorylated NF-κB was significantly increased only in nuclear fractions from α-syn-tg mice brain homogenates. Similar to results observed by immunofluorescence, the level of phosphorylated NF-κB was significantly reduced by HE administration in α-syn-tg mice. A positive interactive effect of HE treatment on the level of phosphorylated-NF-κB ($F_{interaction\ (1,\ 16)}$=11.55, p=0.0037) was confirmed by two-way ANOVA. Taken together, these results suggest that administration of HE decreases neuroinflammation through modulation of NF-κB activity in a mouse model of PD.

Administration of HE prevented neurodegeneration in a mouse model of PD. The loss of TH-positive neurons was significantly decreased by administration of HE in α-syn-tg mice. Behavioral defect also was ameliorated by HE administration in α-syn-tg mice. Furthermore, HE inhibits the activity of NF-κB, which results in decrease of neuroinflammation in α-syn-tg mice.

Intraneuronal accumulations of α-synuclein aggregates are typical pathological features of PD. Studies have demonstrated that these deposits are not only pathological but also playa critical role in the onset and development of PD. Recent studies have shown that neuronal accumulation of α-synuclein can be affected by multiple intra- and extra-neuronal factors, including genetic defects, dysfunction of protein quality control systems, secondary structural alterations, and exposure to environmental toxicants. In addition, neuroinflammation has been suggested as a promotable factor for α-synuclein aggregates in neurons. Administration of HE reduced the neuronal accumulation of α-synuclein in a model of PD. Since the levels of α-synuclein mRNA were not affected by administration of HE, activation of the intraneuronal autophagy process may be regulated by neuroinflammation.

The mechanism by which microglia-mediated neuroinflammation affects neuronal accumulation of α-synuclein aggregates is still unclear. However, recent studies have shown that some pro-inflammatory cytokines inhibit autophagy, an efficient intracellular process for α-synuclein elimination. For example, IL-10 inhibits starvation-induced, rapamycin-induced, and lipopolysaccharide-induced autophagy in murine macrophages. In addition, IL-4 and IL-13 inhibit both starvation-induced and IFN-γ induced autophagosome formations in human and murine macrophages. These observations suggest that cytokines from activated microglia may inhibit the autophagy process of neighboring neurons in the brain, thereby resulting in neuronal α-synuclein accumulation. Considering the previous results together with the present invention, the administration of HE decreases neuronalaccumulation of α-synuclein via reduction of neuroinflammation in a model of PD leading to increased autophagic degradation of α-synuclein.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A method for treating Parkinson's disease in a human, comprising:
administering to said human an effective amount of a compound having a formula:

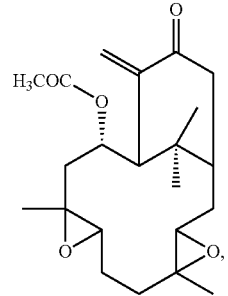

wherein said effective amount is sufficient to ameliorate at least one symptom of Parkinson's disease.

2. The method of claim 1, wherein said compound is present in a dosage form selected from a group consisting of tablets, fine granules, capsules, cachets, troches, lozenges, dispersions, suppositories, ointments, cataplasms, pastes, powders, dressings, creams, piasters, solutions, patches, aerosols, gels, suspensions, and injections.

3. The method of claim 1, wherein said compound is active in decreasing neuronal accumulation of α-synuclein.

4. The method of claim 1, further comprising the steps of monitoring said human for a reduction in said at least one symptom of Parkinson's disease.

5. The method of claim 1, wherein said compound is administered in a dose from 0.1 mg/kg/day to 200 mg/kg/day.

6. The method of claim 1, wherein said compound is active in decreasing phosphorylated NFκB levels in the brain.

* * * * *